United States Patent
Liu et al.

(10) Patent No.: US 8,357,092 B2
(45) Date of Patent: Jan. 22, 2013

(54) INTEGRATED USB CONTROL PANEL FOR A MEDICAL DIAGNOSIS SYSTEM AND A MEDICAL DIAGNOSIS SYSTEM USING THE SAME

(75) Inventors: Zhaoquan Liu, Nanshan (CN); Qianquan Han, Nanshan (CN); Zhe Wang, Nanshan (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1339 days.

(21) Appl. No.: 11/605,605

(22) Filed: Nov. 29, 2006

(65) Prior Publication Data
US 2008/0081981 A1  Apr. 3, 2008

(30) Foreign Application Priority Data
Aug. 7, 2006  (CN) .......................... 2006 1 0062025

(51) Int. Cl.
*A61B 8/00* (2006.01)
(52) U.S. Cl. ..................................... 600/437
(58) Field of Classification Search ................ 600/407, 600/437; 710/1, 9, 10, 104
See application file for complete search history.

(56) References Cited

U.S. PATENT DOCUMENTS

| | | | |
|---|---|---|---|
| 5,050,613 A * | 9/1991 | Newman et al. | 600/483 |
| 6,592,520 B1 * | 7/2003 | Peszynski et al. | 600/437 |
| 7,038,665 B1 | 5/2006 | Pandana | |
| 2001/0025882 A1 * | 10/2001 | Coulier | 235/380 |
| 2003/0103665 A1 * | 6/2003 | Uppaluri et al. | 382/131 |
| 2005/0088834 A1 * | 4/2005 | Milan | 361/810 |
| 2007/0225590 A1 * | 9/2007 | Ramos | 600/407 |
| 2008/0161688 A1 * | 7/2008 | Poland | 600/437 |

FOREIGN PATENT DOCUMENTS

| | | |
|---|---|---|
| CN | 1572235 | 2/2005 |
| CN | 2696547 Y | 5/2005 |
| CN | 1795430 | 6/2006 |

* cited by examiner

*Primary Examiner* — Elmer Chao
(74) *Attorney, Agent, or Firm* — Kory D. Christensen; Stoel Rives LLP

(57) ABSTRACT

This invention discloses a medical diagnosis system a control panel thereof. According to this invention, a USB technology is utilized to perform input via the human-computer interface of the medical diagnosis system. Except for completely compatible with the standard alphanumeric keys portion, the control panel further comprises specific function modules for the medical diagnosis system and the trackball module. The connection of all function modules of the control panel are implemented by one physical interface. Universal alphanumeric keys and the trackball, as well as the specific function modules for the medical diagnostic equipment, are integrated into a whole body, and communicate with the upper computer (PC) via one physical interface, thereby complexity in connecting the peripheral devices of the human-computer interface is reduced, Plug-and-Play can be supported, and the use of it is easier and more convenient.

10 Claims, 2 Drawing Sheets

INTEGRATED USB CONTROL PANEL FOR A MEDICAL DIAGNOSIS SYSTEM AND A MEDICAL DIAGNOSIS SYSTEM USING THE SAME

BACKGROUND OF THE INVENTION

The present invention relates to an integrated USB control panel for a medical diagnosis system and a medical diagnosis system using the same. Ultrasonic diagnostic equipment is one of the three main imaging equipments in a hospital. As a human-computer interface device for an ultrasonic diagnostic equipment, a control panel comprises universal alphanumeric keys, adjustment potentiometer for adjusting TGC (TGC Sliders), an encoder for adjusting gains or menu knobs, a trackball for moving cursors, and function keys (for example, a Cineloop) specific to an ultrasonic equipment, as well as a backlight control means for a control panel. Compared with universal PCs in terms of functions, the alphanumeric keys are similar to PC keyboards, the trackball is similar to a PC mouse, while all the other means are ultrasound specific input devices.

In the configurations of existing products commercial available, a microcontroller unit (MCU) and a Complex Programmable Logic Device (CPLD) are utilized to control the operation of the inside circuit of a board, and its communication with an upper computer is carried out via a RS232 interface. With the rapid development in capability of PCs, the upper computer is gradually replaced by an x86 industrial control board. During transition of the configurations, the control panel with the RS232 interface suffers from such a dilemma that a basic input/output system (BIOS) cannot be set upon startup of the x86.

To make the setting of the BIOS available, an usual solution in the prior art is to divide a control panel into a plurality of function modules, wherein the alphanumeric keyboard is replaced with a universal PC keyboard, for example, a PC keyboard utilizing a PS/2 or USB interface, and the other portions communicate via a RS232 interface, so as to meet requirements of the configuration with minimum modification.

However, the prior art is disadvantageous in two aspects as follows.

I. Since at least one RS232 serial interface line and one PS/2 line (or USB line) must be provide in the configuration of the prior art, interfaces with PC modules are increased. Meanwhile, the design of the medical diagnosis system is limited due to the fact that the alphanumeric keys are replaced with the universal PC keyboard whose shape and mechanical size may bring adverse influence on the design.

II. As conventional serial/parallel interfaces are being replaced gradually by Universal Serial Buses (USBs), there is a trend that RS232 interfaces will be replaced by USB interfaces. For example, serial/parallel interfaces can no longer be supported in high-end industrial control modules, such as COM Express Modules of PIGMG Specification.

BRIEF SUMMARY OF THE INVENTION

In view of above disadvantages, an objective of the present invention is to provide a medical diagnosis system and a control panel thereof capable of connecting the control panel to the upper computer with strong versatility, good adaptability and low cost.

To carry out the above objective, according to one aspect of preferred embodiments of the present invention, a control panel for a medical diagnosis system is provided. The control panel comprises: a control module for controlling an operation of the control panel as a whole; a key array which is connected to the control module and includes an alphanumeric key portion and a function key portion; a trackball module which is connected to the control module for performing movement of a cursor and press of left/right keys; a USB communication module which is connected to the control module for performing communication between the control module and the medical diagnosis system; and a USB interface which is connected to the USB communication module for connecting the control panel with the medical diagnosis system. Wherein, data generated from press of the alphanumeric keys portion and data generated from movement of the trackball portion are transmitted via a single endpoint, and wherein a flag code to be distinguished by the medical diagnosis system is further provided in each of the data generated from press of the alphanumeric keys portion and data generated from movement of the trackball portion.

Preferably, the control panel according to the present invention further comprises a TGC adjustment module which is connected to the control module for performing different depths of time gain compensation (TGC) for ultrasound images.

Preferably, the control panel according to the present invention further comprises an encoder module which is connected to the control module for performing selection for function menus.

According to another aspect of preferred embodiments of the present invention, a medical diagnosis system using the control panel according to the present invention is provided. The medical diagnosis system comprises an upper computer and a medical diagnostic equipment function module. The control panel, the upper computer and the medical diagnostic equipment function module are connected with each other. The alphanumeric keys portion and the trackball module of the control panel are both driven directly by an operating system of the upper computer, and the medical diagnostic equipment function module is driven by a corresponding driver preinstalled in the upper computer.

Preferably, in the medical diagnosis system according to the present invention, the medical diagnostic equipment function module comprises function keys and/or a TGC adjustment potentiometer.

Preferably, in the medical diagnosis system according to the present invention, the alphanumeric keys portion is enumerated as a USB standard keyboard of PCs upon the upper computer entering into a basic input/output system.

Preferably, in the medical diagnosis system according to the present invention, the medical diagnostic equipment function module transmits data in a custom format to the upper computer.

The medical diagnosis system according to the present invention utilizes USB technology to perform input via the human-computer interface of the medical diagnosis system. Further, the control panel according to the present invention is completely compatible with the standard alphanumeric keys portion, and further comprises function modules specific to the medical diagnosis system and the trackball module. The connections of all function modules of the control panel are implemented by one physical interface (i.e. USB interface) so as to simplify the connections. The universal alphanumeric keys and the trackball, as well as the function modules specific to the medical diagnostic equipment are integrated into a whole body, and communicate with the upper computer (PC) via one physical interface (i.e. USB interface), thereby complexity in connecting peripheral devices of the human-computer interface is reduced. Further, since Plug-and-Play can be supported, the convenience in utilization is much improved. Without limitation on the universal PC keyboards, the control panel according to the present invention can be integrated into a whole body, so that the designs of the control panel and the medical diagnosis system using the control panel will not limited by the universal PC keyboards but be flexible and adaptable. Therefore the variety of the designs of the control panel and the medical diagnosis system using the control panel is enhanced greatly.

DETAILED DESCRIPTION OF THE INVENTION

A further detail description of the invention will be given below through the preferred embodiments with reference to the accompanying drawings.

Figure 1:
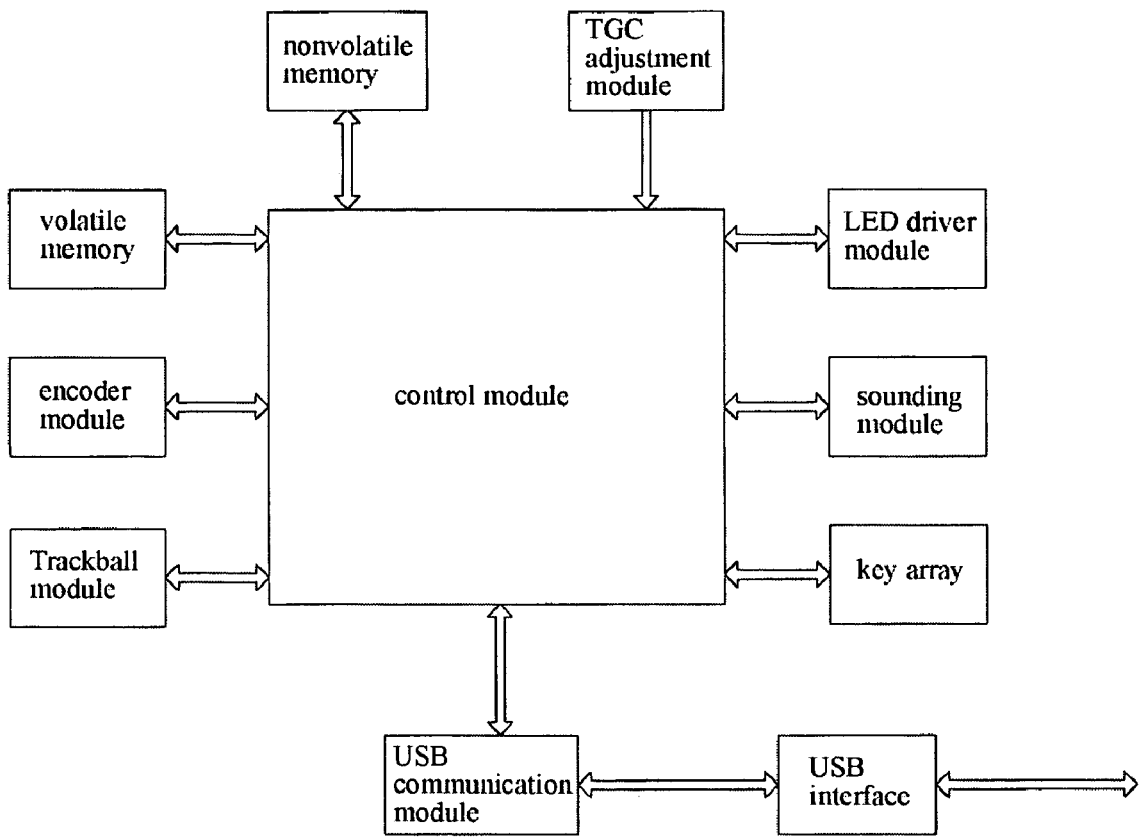
FIG. 1 is a functional block diagram showing the circuit of a control panel according to a preferred embodiment of the invention.

FIG. 1 is a functional block diagram showing the circuit of a control panel according to a preferred embodiment of the invention, which is adaptive for a medical diagnosis system in which an ultrasonic diagnosis front end equipment is used. As shown in FIG. 1, the control panel according to the embodiment comprises: a control module for coordinating and controlling a normal operation of each module by using an embedded soft-core processor; a key array including alphanumeric keys and function keys, wherein whether or not one or more keys among the key array are pressed can be detected by the control module; a sounding module for performing sounding of pressing the one or more keys, i.e., performing sounding when the one or more keys are pressed; a LED driver module for performing a backlight function of the alphanumeric keys and a backlight function and a two-color indication function of the function keys; a TGC adjustment module for performing different depths of time gain compensation (TGC) for ultrasound images, a nonvolatile memory for storing configuration files of FPGA (field programmable gate array) and firmware of the embedded soft-core processor; a volatile memory using as a storage space of the embedded soft-core processor into which the firmware of the embedded soft-core processor may be loaded such that an executing speed of the embedded soft-core processor can be enhanced; an encoder module for performing selection for function menus and the like; a trackball module for performing movement cursors and press of left/right keys; and a USB communication module and a USB interface for performing communications between the control module and the upper computer.

Figure 2:
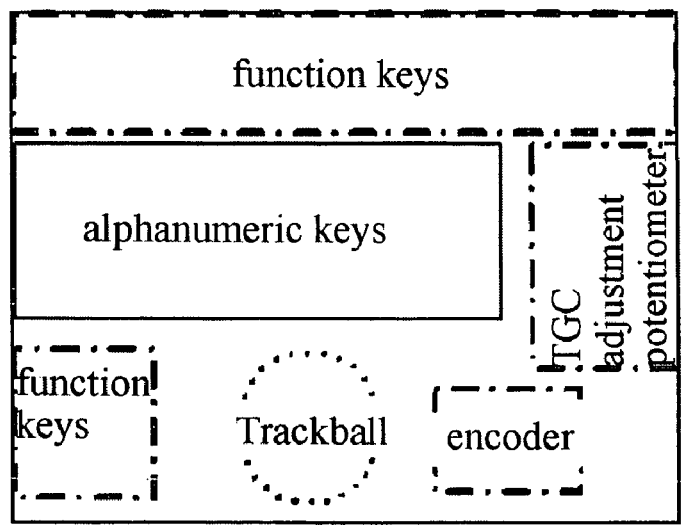
FIG. 2 is a diagram showing an arrangement of respective function modules of the control panel according to a preferred embodiment of the invention.

To ensure that various functions can be carried out via one physical USB interface, the control panel is divided into three portions as follows. The first portion is constituted of alphanumeric keys, which can be utilized as usual both in setting the BIOS and after the upper computer (PC) has entered into an operating system (Windows). In the first portion, the upper computer (PC) can directly use drivers provided by the operating system (Windows) without any driver exclusively provided. The second portion is constituted of the trackball, which can be utilized only after the upper computer (PC) has entered into the operating system. In the second portion, the upper computer (PC) can also directly use drivers provided by the operating system (Windows) without any driver exclusively provided. The third portion is constituted of various modules specific to ultrasonic diagnostic equipments, such as various function keys, an encoder, a TGC adjustment potentiometer, various signal indication LEDs and the like. The third portion can be utilized only after the upper computer (PC) has entered into the operating system and the corresponding drivers thereof are installed, because the operating system (Windows) can not provide drivers for this portion. The arrangements of the above portions on the control panel are shown in FIG. 2. In this figure, the portion surrounded by solid lines indicates the alphanumeric keys; the portion surrounded by the circular dashed line indicates the trackball; and the portion surrounded by the chain dotted lines indicates the function keys, the encoder, and the TGC adjustment potentiometer and the like. Incidentally, LEDs for backlights of the keys are not shown in FIG. 2 since they are arranged around all the keys and the encoder.

Figure 3:
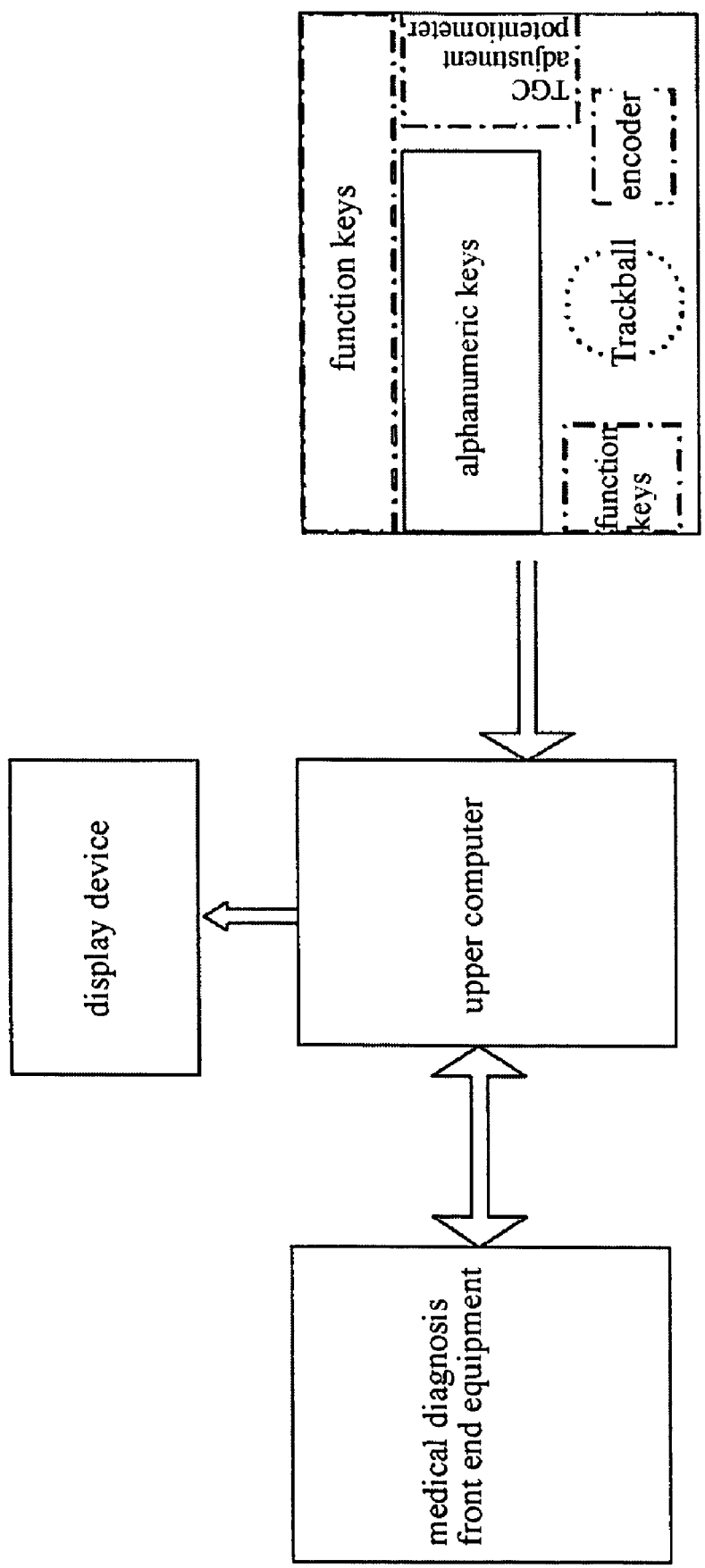
FIG. 3 is a skeleton diagram showing the structure of the medical diagnosis system according to a preferred embodiment of the invention.

Now Referring to FIG. 3, a structural skeleton diagram of the medical diagnosis system according to an embodiment of the invention is shown. The medical diagnosis front end equipment in this embodiment is an ultrasonic diagnostic front end equipment which is connected to an upper computer. The connection of the control panel according to the embodiment of this invention with the upper computer is carried out via a USB interface. The above described first and second portions belong to the Human Interface Device which is one kind of the USB devices, thereby they utilize a single endpoint. To ensure that the first portion can be operated as usual when the upper computer (PC) is entering into BIOS, the control panel is enumerated only as a USB standard keyboard of PCs in the BIOS. At this time, the control panel operates only in response to the operations of the alphanumeric keys, while does not operate in response to the operations of other devices such as the trackball and adjustment potentiometer. The transmission format for data generated by pressing the keys is shown in Table 1.

TABLE 1

Transmission Format for data generated by pressing alphanumeric keys in the BIOS

| BYTE7 | BYTE6 | BYTE5 | BYTE4 |
|---|---|---|---|
| Keycode6 | Keycode5 | Keycode4 | Keycode3 |
| BYTE3 | BYTE2 | BYTE1 | BYTE0 |
| Keycode2 | Keycode1 | Reserved | Modifier Keys |

In the above table, BYTE[7:2] represents keycodes, BYTE1 is reserved, and Modifier Keys in BYTE0 are used to represent combination keys such as Ctrl, Shift, Alt and the like, and the particular definitions thereof are shown in Table 2.

TABLE 2

Contents Represented By Modifier Keys

| Bit 7 | Bit 6 | Bit 5 | Bit 4 | Bit 3 | Bit 2 | Bit 1 | Bit 0 |
|---|---|---|---|---|---|---|---|
| Reserved | Reserved | Reserved | Reserved | Reserved | Alt | Shift | Ctrl |

Once the upper computer (PC) has entered into the operating system, the usability of all the three portions described above will be available. Because the alphanumeric keys and the trackball transmit data via a single endpoint, one byte is added into each of the data as a flag code for distinguishing data type, so that the upper computer (PC) can correctly distinguish data of the alphanumeric keys from data of the trackball. That is, for example, in the data generated from pressing alphanumeric keys, one more byte is added to forefront of Table 1, and the last byte, BYTE0, is taken as the flag code for distinguishing data type. The data format is shown in Table 3.

TABLE 3

Transmission Format for data generated from pressing the Alphanumeric Keys in Operating System (Windows)

| BYTE8 | BYTE7 | BYTE6 | BYTE5 |
|---|---|---|---|
| Keycode6 | Keycode5 | Keycode4 | Keycode3 |
| BYTE4 | BYTE3 | BYTE2 | BYTE1 |
| Keycode2 | Keycode1 | Reserved | Modifier Keys |
| BYTE0 | | | |
| 00H | | | |

Transmission format for data of the trackball is shown in Table 4.

TABLE 4

Transmission Format for data of the trackball

| BYTE3 | BYTE2 | BYTE1 | BYTE0 |
|---|---|---|---|
| Track ball keys | Y offset | X offset | 01H |

The Track ball keys in BYTE3 of the above table are used to represent keys of the trackball, and the particular definitions thereof are shown in Table 5.

TABLE 5

Content Represented By Keys of trackball

| Bit7–Bit3 | Bit2 | Bit1 | Bit0 |
|---|---|---|---|
| Default value 0 | Button 3 | Button 2 | Button 1 |

The portions of the function modules specific to the ultrasonic diagnostic system transmit data in custom data format. The upstream data includes the data generated from the adjustment potentiometer, the encoder, and the function keys, as well as the data in response to the upper computer (PC), etc., while the downstream data includes the data for controlling LED indicator. All those data are transmitted in custom data format. Because the portions specific to the ultrasonic diagnostic equipment belong to a kind of a custom USB device, when the USB interface of the control panel has been connected to the upper computer (PC), the upper computer (PC) first performs the enumeration of the USB control panel, and then loads the corresponding driver to ensure that the USB control panel can perform data exchange with the upper computer (PC) correctly. The load of drivers includes the following two cases. In a first case, for the USB control panel installed for a first time, a hardware installation wizard will be shown by the operating system of the upper computer (PC) to indicate that a new USB device is found, and then a corresponding device driver for the USB control panel must be specified and installed. In a second case, for the USB control panel whose device driver has be installed in advance, when it is connected to the upper computer (PC) once again, the driver thereof will be dynamically loaded by the operating system. Thereafter, specific drivers designed for the portions specific to the ultrasonic diagnostic equipment is allocated to the control panel to ensure that the specific portion can perform exact data exchange with the upper computer (PC).

The transmission format for data generated from pressing the custom function keys is shown in Table 6.

TABLE 6

Transmission Format for Data Generated from Pressing Self-Defining Function Keys

| BYTE1 | BYTE0 |
|---|---|
| Keycode | 02H |

The transmission format for data generated from the encoder is shown in Table 7.

TABLE 7

Transmission Format for Data Generated from the Encoder

| BYTE2 | BYTE1 | BYTE0 |
|---|---|---|
| data1 | data0 | 03H |

The transmission format for data of the TGC adjustment module is shown in Table 8. In Table 8, data of the second byte represents a TGC channel number. For example, the number for a first channel is 1, and that for a second channel is 2, and so on. The data of the third byte is data of a corresponding channel.

TABLE 8

Transmission Format for the Data of TGC Adjustment Module

| BYTE2 | BYTE1 | BYTE0 |
|---|---|---|
| data | channel | 04H |

The downstream data includes the data for control signal of the LED indicator and the like. Table 9 shows the transmission format of data for control signal of the LED indicator, wherein the second byte represents a position of a corresponding LED, and the third byte represents a status and brightness level of a corresponding LED. The definition of the bits of data of the signal is shown in Table 10.

TABLE 9

Transmission Format for the Data of Control Signal of LED indicator

| BYTE2 | BYTE1 | BYTE0 |
|---|---|---|
| data | number | 05H |

TABLE 10

| Meanings Represented By the Third Byte of the LED Indicator | | |
|---|---|---|
| Bit7–bit6 | bit5–bit2 | bit1–bit0 |
| Default value 0 | brightness level | LED status |

In this embodiment, a soft-core processor is used as the core of the control module, and programs of the soft-core processor and the logic design data of FPGA are saved in the nonvolatile memory. After the control panel is powered up, FPGA automatically read configuration data from this nonvolatile memory to complete the configuration of FPGA. Once the configuration of FPGA is completed, the PC (Program counter) pointer of the soft-core processor will point to Boot Rom. At this time, the copy of data stored in the nonvolatile memory into the volatile memory will be started. Upon the copy is completed, the PC (Program counter) pointer of the soft-core processor will point to the volatile memory so as to run the whole application program and start the regular operation of the control panel.

Some modules can be added into or omitted from the control panel according to above embodiment so as to enhance or simplify the processing functions of the control panel. More new human computer interaction device of USB type can be designed with the concept of this method. The method can be applied to other products of medical devices, which are similar to medical diagnostic ultrasonic systems, and in which a human computer interaction interface of USB type can be supported by an upper computer, for completing the design of human computer interaction equipments.

What is claimed is:

1. A control panel for a medical diagnosis system, comprising:
   a control module for controlling an operation of the control panel as a whole;
   a key array which is connected to the control module and includes an alphanumeric keys portion and a function keys portion;
   a trackball module which is connected to the control module for performing movement of a cursor and press of left/right keys;
   ultrasound diagnostic equipment modules connected to the control module for transmitting ultrasound diagnostic system control data to an upper computer of the medical diagnosis system;
   a USB communication module which is connected to the control module for performing communication between the control module and the upper computer of the medical diagnosis system; and
   a single USB interface which is connected to the USB communication module for connecting the control panel with the upper computer of the medical diagnosis system, wherein
   the alphanumeric keys portion and the trackball module are each configured to generate input data from a user transmitted to the upper computer in data packets via a single logical transmission endpoint, and wherein the control module is configured to append a flag code comprising a distinguishing byte to each data packet of the input data generated from the alphanumeric keys portion and input data generated from the trackball module, the flag code being configured to be utilized by the upper computer to distinguish the input data generated from the alphanumeric keys portion from the input data generated from trackball module.

2. The control panel according to claim 1, further comprising a TGC adjustment module which is connected to the control module for performing different depths of time gain compensation (TGC) for ultrasound images.

3. The control panel according to claim 1, further comprising an encoder module which is connected to the control module for performing selection for function menus.

4. The control panel according to claim 2, further comprising an encoder module which is connected to the control module for performing selection for function menus.

5. A medical diagnosis system using the control panel according to claim 1, further comprising a medical diagnostic equipment function module, wherein the control panel, the upper computer and the medical diagnostic equipment function module are connected with each other, wherein the alphanumeric keys portion and the trackball module of the control panel are both driven directly by an operating system of the upper computer, and the medical diagnostic equipment function module is driven by a corresponding driver preset by the upper computer.

6. The medical diagnosis system according to claim 5, wherein the medical diagnostic equipment function module comprises function keys and/or a TGC adjustment potentiometer.

7. The medical diagnosis system according to claim 5, wherein the alphanumeric keys portion is enumerated as a USB standard keyboard of PCs upon the upper computer entering into a basic input/output system.

8. The medical diagnosis system according to claim 6, wherein the alphanumeric keys portion is enumerated as a USB standard keyboard of PCs upon the upper computer entering into a basic input/output system.

9. The medical diagnosis system according to claim 5, wherein the medical diagnostic equipment function module is configured to format data transmitted to the upper computer.

10. The medical diagnosis system according to claim 6, wherein the medical diagnostic equipment function module is configured to format data transmitted to the upper computer.

* * * * *